United States Patent [19]

Scharf

[11] Patent Number: 5,098,304
[45] Date of Patent: Mar. 24, 1992

[54] DENTAL MATERIALS AND PROCESS UTILIZING ETCHED SILANATED GLASS FIBER

[76] Inventor: Jonathan Scharf, 364-A7 St. Andrews Rd., Glenmoore, Pa. 19343

[21] Appl. No.: 524,242

[22] Filed: May 15, 1990

[51] Int. Cl.⁵ .............................................. A61C 5/00
[52] U.S. Cl. .................................... 433/215; 433/180
[58] Field of Search ................. 433/215, 180, 181, 24, 433/226

[56] References Cited

U.S. PATENT DOCUMENTS

| | | |
|---|---|---|
| 2,700,010 | 1/1955 | Balz . |
| 3,637,550 | 1/1972 | Sprauer . |
| 4,172,323 | 10/1979 | Orlowski .......................... 433/180 |
| 4,274,907 | 6/1981 | Vig et al. . |
| 4,292,236 | 9/1981 | Ibsen et al. . |
| 4,415,404 | 11/1983 | Riegel . |
| 4,433,960 | 2/1984 | Garito et al. ........................ 433/180 |
| 4,473,353 | 9/1984 | Greggs . |
| 4,632,660 | 12/1986 | Jurim .................................. 433/215 |
| 4,654,007 | 3/1987 | Sigler et al. . |
| 4,710,217 | 12/1987 | Bailey et al. . |
| 4,728,291 | 3/1988 | Golub . |
| 4,793,809 | 12/1988 | Sigler et al. . |
| 4,799,888 | 1/1989 | Golub . |

OTHER PUBLICATIONS

"Effect of porcelain surface treatment on the bond to composite", The Journal of Prosthetic Dentistry, vol. 60, No. 3, Sep. 1988—Alton M. Lacy, M.S., Ph.D., D.D.S.; Jose LaLuz, Larry G. Watanabe, B.S., and Mark Dellinges, D.D.S.

"In vitro effect of topical fluoride on dental porcelain", The Journal of Prosthetic Dentistry, vol. 55, No. 3, Mar. 1986—Richard C. Wunderlich, D.D.S., M.S., and Peter Yaman, D.D.S., M.S.

"DICOR ® Surface Treatments for Enhanced Bonding", J Dent Res, vol. 67, No. 6, Jun. 1988—L. F. Bailey and R. J. Bennett.

"Decrease in reflectance of porcelains treated with APG gels"—Dental Materials, vol. 4, pp. 289-295, 1988—Gonzalez, E., Naleway C. A., Fan P. L., Jaselskis T.

"Etching Effect of topical fluorides on dental porcelains: A Preliminary Study", J. Canad Dent Assn, No. 6, 1973—D. J. Gau, DDS, E. A. Krause.

"Effect on air-powder abrassive instrument on Porcelain", Journal of Prosthetic Dentistry, vol. 60, No. 4, Oct. 1988—Robert L. Cooley, D.M.D., M.S.; Richard M. Lubow, D.M.D., M.S.; Frederic H. Brown, D.M.D., M.S.

"Effects of topical fluorides on five low-fusing dental porcelains"—The Journal of Prosthetic Dentistry, vol. 52, No. 3, Sep. 1984—Daniel P. Copps, D.D.S.; Alton M. Lacy, Ph.D., D.D.S., Thomas Curtis, D.D.S.; and John E. Carman, D.D.S.

"The Silk Wrap Technique for Composite Bonding", The New York State Dental Journal, vol. 53, No. 5, May, 1987—Jeff Evans Golub, D.D.S.

"The Manhattan bridge: a new silk-wrap technique", Dental Abstracts, vol. 32, No. 2, Feb. 1987—J. E. Golub.

"Smile Makeovers", McCall's magazine, Feb. 1987—Golub.

Single page entitled "Silkwrap The Silk-Bonded Restorative" by Dentique, Inc.

"Porcelain-to-composite bond Strengths using four organosilane materials", Journal of Prosthetic Dentistry, vol. 61, No. 2, Feb. 1989—J. H. Bailey, D.D.S.

(List continued on next page.)

Primary Examiner—Gene Mancene
Assistant Examiner—Adriene B. Lepiane
Attorney, Agent, or Firm—Michael F. Petock

[57] ABSTRACT

The composite resin reinforcement system for use in dental operations provides improved strength by the use of etched glass fiber material which is then silanated with an organo-functional silane and utilized in a composite resin in the dental operation. The glass fiber material may be uniform or random mesh, rope, thread or other suitable shapes. The etched silanated glass fiber material is utilized in the composite resin for restoring and/or splinting teeth.

16 Claims, 2 Drawing Sheets

OTHER PUBLICATIONS

"Composite Resin Repair of Porcelain Using Different Bonding Materials", *Operative Dentistry*, vol. 13, pp. 114–118—Gregory et al.

"Tensile Bond Strengths of Five Porcelain Repair Systems", *Operative Dentistry*, vol. 13, pp. 162–167, 1988—Cochran et al.

"Bond strengths of intraoral porcelain repair materials", *The Journal of Prosthetic Dentistry*, vol. 61, No. 3, Mar. 1989—Diaz-Arnold et al.

"Repairing Porcelain" under heading *The Reviews* of a monthly update to *Reality Now/The information source of esthetic dentistry*, No. 3, Mar. 1989, by Diaz-Arnold, A. M. et al. (Subtitle: Are Silanes Ready Different?).

"Luting interfaces and materials for etched porcelain restorations. A status report for the American Journal of Dentistry", *American Journal of Dentistry*, vol. 1, No. 5, Oct. 1988—Sheth and Jensen.

*Theory of Mechanisms of Silane Coupling Agents in Glass Reinforced and Filled Thermoplastic and Thermosetting Resin Systems* by Sterman and Marsden/Union Carbide Corporation/Adhesion Promoters.

*Organofunctional Silanes—A Profile* by Union Carbide Corporation/Silicones and Urethane Intermediates.

"Functions, applications and advantages of silane coupling agents" reprinted from *Plastics Compounding* for Resin Producers, Formulators and Compounds, Jul.-/Aug. 1978 by James Marsden for Union Carbide Corp.

Brochure entitled *Union Carbide Silicones Organofunctional Silanes Product Information*—"Union Carbide Organofunctional Silane A-1130", Form F-4770, 12/80-4M.

Abstracts from *Craniofacial Biology/Dental Materials*, p. 245, Nos. 1105–1112.

Abstracts from IADR-ADDR Abstracts 1985, p. 296, Nos. 1090, 1092, 1093, 1095, 1096.

Book entitled *Reality/The information source for esthetic dentistry*, vol. 4, No. 1, 1989, edited by Esthetic Dentistry Research Group, pp. 80–81, 145–148, 205–206.

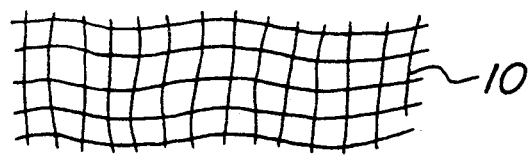
FIG. 1
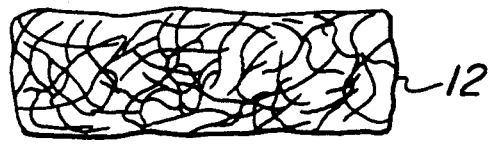
FIG. 2
FIG. 3
FIG. 4
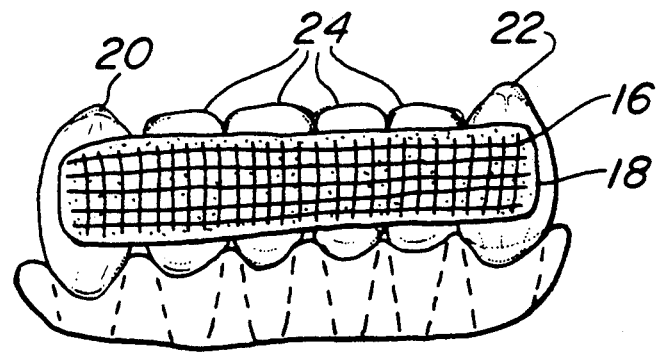
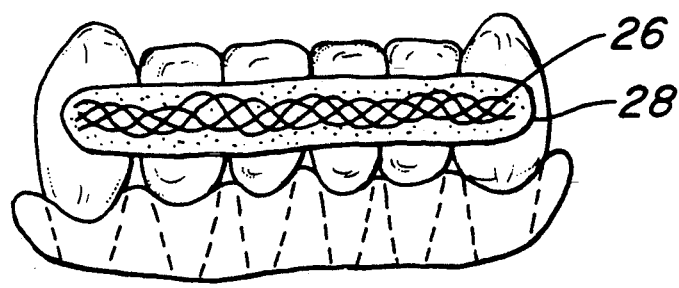
FIG. 5

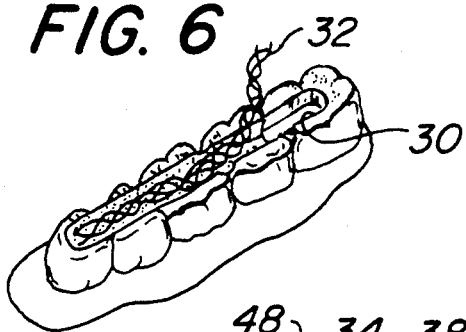
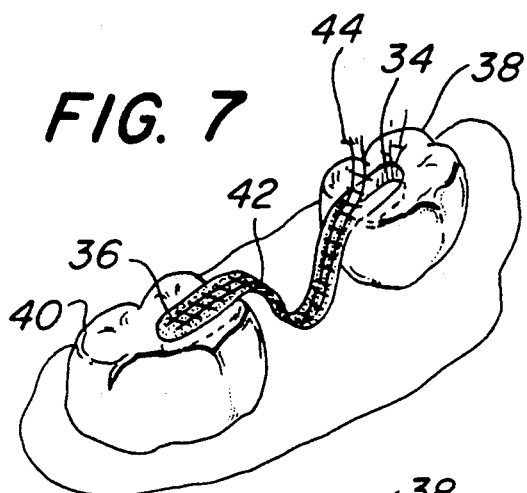
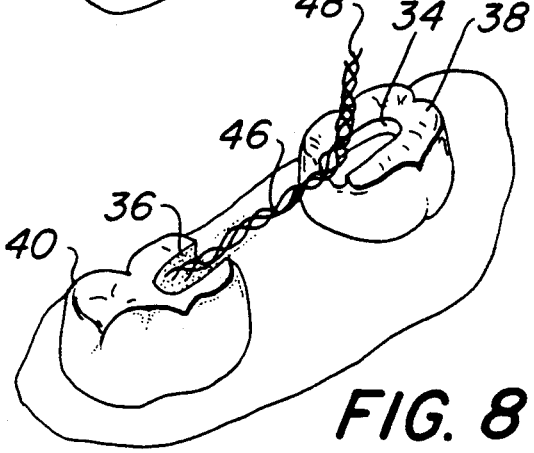
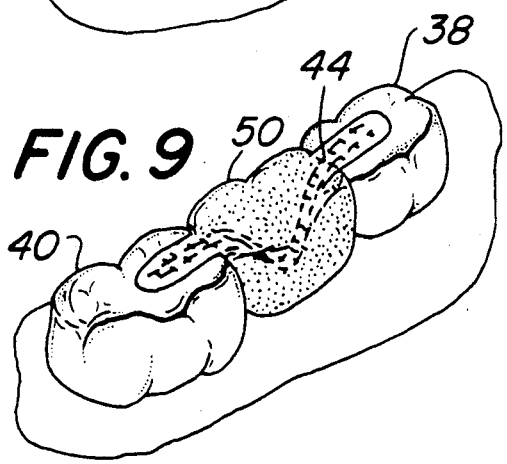
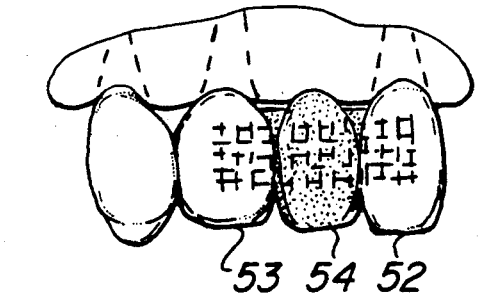
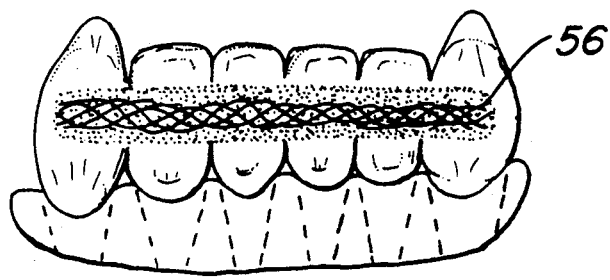

DENTAL MATERIALS AND PROCESS UTILIZING ETCHED SILANATED GLASS FIBER

BACKGROUND OF THE INVENTION

The present invention relates to an improvement in the field of prosthetic dentistry and more particularly to the field of restorative and splinting operations in the field of dentistry using various resins.

Use of various composite resins in dentistry to restore one or more teeth and to improve the cosmetic appearance of the teeth has been known for some time and has been finding greater use in dentistry. However, the use of composite resins, such as macrofills and microfills in dentistry have had some drawbacks such as an inability to handle stress in particular cases, for example such as in cantilevering and in the case of bruxers. However, recently, an attempt has been made to eliminate the shortcomings of the use of composite resins by reinforcing the composite resin with a silk fabric. See Golub, *The Silk Wrap Technique For Composite Bonding, The New York State Dental Journal*, May 1987, Volume 53, No. 5, pp. 28-29, and U.S. Pat. No. 4,728,291-Golub and U.S. Pat. No. 4,799,888—Golub.

However, applicant herein has invented a new and improved composite resin reinforcement system for use in dental operations which provides improved strength characteristics.

SUMMARY OF THE INVENTION

Briefly and basically, in accordance with the present invention, applicant has invented a new and improved means for reinforcing composite resin systems for restoring and/or splinting teeth which utilizes an etched glass fiber material which is treated with an organo-functional silane. The etched glass fiber material is preferably etched with an acid such as hydrofluoric acid or 1.23% acidulated phosphate fluoride, although any other suitable etchant may be utilized which will be effective in etching glass and particularly glass fiber material.

The glass fiber material may preferably be a uniform mesh, a random mesh or a rope or thread type material which may be utilized in dental operations as described hereinafter. Of course, other suitable forms of glass fiber material may be utilized in the particular dental application. Such glass fiber products are commercially available under the FIBERGLAS trademark of Owens-Corning Corp. As well as from others. Any of a number of organo-functional silanes may be utilized to act as coupling agents between the glass fiber material and the composite resin. The formation of a chemical bridge between the coupling agents and a glass substrate requires both a reactive silane and a reactive site on the glass surface. In fiber glass reinforcement, the reactive sites are the silanols on the glass surface. The silane coupling agents react with these surface silanols through hydrolyzable groups bonded to the silicon atom of the coupling agent molecule. These reactive groups can be —OH, —Cl, —OR, —OAc or —NR$_2$. Some of the organo-functional silanes which may be utilized in practicing the invention include Vinyltrichlorosilane, Vinyltriethoxysilane, Vinyl-tris(beta-methoxyethoxy)silane, gamma-Methacryloxypropyltrimethoxysilane, beta-(3,4-Epoxycyclohexyl)-ethyl-trimethoxysilane, gamma-Glycidoxypropyltrimethoxysilane, gamma-Aminopropyltriethoxysilane, and N-beta-(aminoethyl)-gamma-aminopropyltrimethoxysilane, as well as various commercially available silane coupling agents sold primarily to dentists under various trademarks.

In accordance with the present invention, the process of the present invention may be carried out for restoring or stabilizing one or more teeth comprising the steps of etching a material comprised of a glass fiber with an etchant, applying an organo-functional silane to the etched material and reconstructing or stabilizing one or more teeth utilizing the etched silanated glass fiber embedded in a resin. The resin may be any one of the various composite resins well known in the art of dentistry as selected by the dentist. As described above, the etching is commonly done by hydrofluoric acid or 1.23% acidulated phosphate fluoride, which is also believed to perform the etching through the formation of hydrofluoric acid. As described more fully hereinafter, various types of mesh or woven thread or rope may be utilized to reconstruct tooth surfaces, reconstruct missing teeth, create bridges, enable orthodontic applications and/or perform various types of splinting, including post orthodontic. For example, in some cases a glass fiber mesh or rope embedded in a resin may be utilized to create a periodontal splint. Such splinting may be done by embedding the etched glass fiber material in a resin along the surface of the teeth or by creating a channel in the enamel of a series of teeth through which the glass fiber rope is embedded with the composite resin. In other cases, a missing tooth may be replaced by utilizing an etched silanated glass rope embedded in the teeth adjacent to the space of the missing tooth, which etched silanated glass fiber rope may be either straight or curved, and which is then utilized as the base on which a tooth replica may be formed from a composite resin by appropriate shaping. Such creation of a missing tooth may be either in the anterior or posterior portion of the mouth and such periodontal splinting may be performed in the anterior or posterior portion of the mouth between teeth not requiring such periodontal splinting.

BRIEF DESCRIPTION OF THE DRAWINGS

For the purpose of illustrating the invention, there are shown in the drawings forms which are presently preferred; it being understood, however, that this invention is not limited to the precise arrangements and instrumentalities shown.

FIG. 1 is a plan view of a uniform mesh comprised of glass fiber material which may be utilized in practicing the present invention.

FIG. 2 is a plan view of a random mesh comprised of glass fiber material which may be utilized in practicing the present invention.

FIG. 3 is a plan view of a woven thread or rope comprised of glass fiber material which may be utilized in practicing the present invention.

FIG. 4 is an elevation view of periodontal splinting utilizing glass fiber uniform mesh applied to mandibular anterior teeth illustrating one of many possible uses of the present invention in the practice of dentistry.

FIG. 5 is an elevation view of periodontal splinting utilizing glass fiber random mesh applied to mandibular anterior teeth illustrating one of many possible uses of the present invention in the practice of dentistry.

FIG. 6 is a view in perspective of periodontal splinting utilizing glass fiber rope applied to posterior teeth illustrating one of many possible uses of the present invention in the practice of dentistry.

FIGS. 7, 8 and 9 are views in elevation of steps in the process of a posterior tooth replacement utilizing a glass fiber rope as an illustration of another possible use in dentistry of the present invention.

FIGS. 10 and 11 are elevation views of maxillary anterior teeth illustrating steps in a tooth replacement utilizing a uniform glass fiber mesh in accordance with the present invention and illustrating another possible use wherein FIG. 10 is a lingual view and FIG. 11 is a labial view.

FIG. 12 is an elevation view of maxillary anterior teeth utilizing glass fiber rope in orthodontic retention and post treatment stabilization to illustrate another possible one of many uses of the present invention in dentistry.

DETAILED DESCRIPTION OF THE PREFERRED EMBODIMENTS

The present invention is directed to a new improved means and method for reinforcing composite resin systems for restoring and/or splinting teeth which utilizes glass fiber material, sometimes referred to as FIBERGLAS, which is a trademark of Owens Corning Corp. In accordance with the present invention, the glass fiber material may be in any form, and is commonly available and utilized in the form of a uniform mesh, a random mesh and thread or rope forms. The glass fiber material is a strong material which provides significant improvement in the strength of the reinforced composite resin.

In order to enhance the bonding of the fiber glass to the composite resin, the fiber glass material is first etched and then treated with an organo-functional silane prior to the application of the composite resin. The etched fiber glass is preferably etched with an acid, such as hydrofluoric acid or 1.23% acidulated phosphate fluoride (APF). The composite resin may be any of the well known composite resins currently being utilized in the practice of dentistry today including those known as microfill, macrofill and hybrid resins, and these are well known in this art. For example, see *Reality/The information source for esthetic dentistry*, Reality Publishing Company, 1989.

The etching of the fiber glass produces a roughened or barbed surface on the glass fibers, which may be observed under the microscope. After the etching is completed, any suitable organo-functional silane may be utilized which is capable of enhancing the bonding between the glass fiber material and the composite resins. A number of these are known and examples of these include the following: Vinyltrichlorosilane, Vinyltriethoxysilane, Vinyl-tris(beta-methoxyethoxy)silane, gamma-Methacryloxypropyltrimethoxysilane, beta-(3,4-Epoxycyclohexyl)-ethyltrimethoxysilane, gamma-Glycidoxypropyltrimethoxysilane, gamma-Aminopropyltriethoxysilane, and N-beta-(aminoethyl)-gamma-aminopropyltrimethoxysilane and commercially available silane coupling agents commonly utilized in dentist's offices including Scotchprime sold by the 3M Company, Clearfil Porcelain Bond sold by J. Morita/Kuraray, Porcelain Primer sold by Kerr, CerinatePrime sold by Den-Mat, Chameleon Bond Enhancer sold by Chameleon, Fusion sold by George Taub Products and Fusion Co., PVS Porcelain Bond sold by Cercom, Silanit sold by Vivadent and Symphony Silane Bond sold by Dental Arts Laboratory. The foregoing commercially available silanes are listed in *Reality/The information source for esthetic dentistry* on pages 80 and 81, supra. In summary, any suitable organo-functional silane coupling agent may be utilized in the practice of the present invention.

The present invention may be utilized in numerous applications in the practice of dentistry, including periodontal splinting, tooth replacement, tooth stabilization, etc. All of these will not be described herein, as such dental operations are well known to those practicing dentistry, i.e. those skilled in the art. However, an illustration of a few of the possible uses will be illustrated herein in connection with the drawing figures. The operations and the specific detail of the actual practice of dentistry will not be repeated herein as they are well known.

Referring now to the drawings wherein like numerals indicate like elements, there is shown in FIG. 1 a uniform mesh 10 which is comprised of a glass fiber material. FIG. 2 illustrates a random mesh 12 comprised of a glass fiber material. There is illustrated in FIG. 3, a woven rope or thread 14 which is comprised of a glass fiber material. Meshes 10 and 12 and rope or thread 14 are all comprised of glass fiber material, which is well known. These are commercially available under the trademark FIBERGLAS of Owens Corning Corp. and from other suppliers. In each case, the fiber glass material would be etched with an acid such as hydrofluoric acid or APF.

Referring now to FIG. 4, there is illustrated periodontal splinting of mandibular anterior teeth utilizing a uniform glass fiber mesh 16 which has been etched and treated with an organo-functional silane and embedded within a composite resin 18. As described previously, the glass fiber mesh 16 may be etched with an acid, preferably hydrofluoric acid or APF, although it is understood that any other acid may be utilized which is effective in etching glass fibers. The periodontal splinting as shown in FIG. 4 is utilized to treat mobile teeth which have lost bone support and/or which have been traumatized. As illustrated in FIG. 4, the etched silanated glass fiber mesh 16 may be embedded in a composite resin 18 bonding together canines 20 and 22 and mandibular incisors 24.

FIG. 5 illustrates a substantially similar application of the present invention wherein a random glass mesh or rope 26 comprised of glass fiber is etched, silanated and embedded in a composite resin 28 as a periodontal splint of the anterior mandibular teeth.

FIG. 6 illustrates another use of the present invention in the practice of dentistry in the form of periodontal splinting of the posterior teeth. As illustrated in FIG. 6, a channel 30 is prepared in the occlusal surfaces of the posterior teeth by well known dental operations. A rope 32 comprised of glass fiber material which has been etched with an acid, such as hydrofluoric acid, and treated with an organo-functional silane as described above, is inserted into the channel and bonded to the tooth by one of the suitable well known composite resins.

FIGS. 7, 8 and 9 illustrate an application of the present invention in posterior tooth replacement wherein the present invention may be utilized to produce a bridge for a missing tooth. As illustrated in FIG. 7, channels 34 and 36 may be prepared in the occlusal surfaces of teeth 38 and 40, respectively, which are immediately adjacent to the missing tooth. A channel may be cut into the enamel of the tooth in a well known manner. The surface of the channel in the tooth may be etched with phosphoric acid and tooth adhesive used to bond etched, silanated, mesh or rope fiber glass in the channel to form a bridge through the space of the missing tooth. This may be provided with a fold 42 in mesh 44 as illustrated in FIG. 7 or more directly bridging the missing tooth space as shown at 46 with fiber glass rope 48 in FIG. 8.

FIG. 9 illustrates a tooth replica or replacement (artificial) tooth formed on etched, silanated fiber glass mesh 44. Alternatively, tooth 50 could be formed on the etched silanated glass fiber rope 48. The etched silanated glass support of fiber glass mesh 44 or rope 48 provides a strong and sturdy base for holding the formed tooth replacement in place.

Referring now to FIGS. 10 and 11, there is shown still another one of the many possible uses of the present invention in the practice of dentistry in the form of an anterior tooth replacement. In a similar manner, channels are prepared in teeth 52 and 53 which are immediately adjacent the missing tooth. Channels are prepared in a well known manner. The teeth are then etched with phosphoric acid, adhesive is placed in the channel and the etched silanated fiber glass mesh is inserted into the channel and the adhesive. This may be tack welded with resin. The formation of the replacement tooth 54 is now built onto the mesh, polymerized and shaped into the form of a tooth.

FIG. 12 illustrates still another one of the many possible uses of the present invention in the practice of dentistry. FIG. 12 illustrates mandibular anterior teeth 30 wherein orthodontic retention and post treatment stabilization are provided by an etched, silanated glass fiber rope or mesh affixed to the etched teeth and embedded in the resin. No preparation, i.e. cutting and channeling, of the tooth is necessary. As illustrated in FIG. 12, the etched fiber glass mesh or rope 56 is applied across the canines and mandibular incisors and embedded in one of the well known composite resins. This process may also be applied to the maxillary teeth.

As a specific example of one application of the present invention, a patient of mine was kicked by a horse resulting in the loss of a mandibular right central incisor. I utilized fiber glass material in the form of a random mesh. I etched the fiber glass mesh with a commercial form of hydrofluoric acid sold under the trademark PORCELETCH by Cosmedent, 5419 North Sheridan Road, Chicago, Ill. 60640. I treated the etched fiber glass with an organo-functional silane sold under the trademark SILANATOR by Cosmedent. I selected and utilized a well known composite resin sold under the trademark ULTRABOND, which was coated with a second well known composite resin sold under the trademark VISARGLAZE. Both the ULTRABOND and VISARGLAZE trademark products are available from Den-Mat Corp., 3130 Skyway Drive, Santa Maria, Calif. 93456. I was able to perform an esthetic and structural restoration of the patient's tooth in 45 minutes with the result being a strong and structurally stable tooth replacement.

In a second situation, two lower incisor teeth had been lost to periodontal disease and the remainder of the lower anterior teeth were mobile. The patient required immediate replacement of the missing teeth and stabilization of the others. Fiber glass material in the form of a uniform mesh was utilized. The fiber glass mesh was etched with a commercially available brand of hydrofluoric acid sold under the trademark PORCELETCH by Cosmedent. The fiber glass mesh was treated with a commercially available organo functional silane sold under the trademark SILANATOR by Cosmedent. I selected a well known macrofill composite resin ULTRABOND which is available from Den-Mat Corp., which was then laminated with a microfill composite resin sold commercially under the trademark DURAFIL by Kulzer Corporation, 10005 Muirlands Boulevard, Irvine, Calif. 92718, which provided improved esthetics. This procedure produced a structurally superior esthetic replacement and the stabilized teeth exhibited no mobility.

In view of the above, the present invention may be embodied in other specific forms without departing from the spirit or essential attributes thereof and, accordingly, reference should be made to the appended claims, rather than to the foregoing specification as indicating the scope of the invention.

I claim:

1. A process for restoring or stabilizing one or more teeth, comprising the steps of:
    etching a material comprised of glass fiber with an etchant;
    applying an organo-functional silane to the etched material; and
    reconstructing or stabilizing one or more teeth utilizing said etched silanated glass fiber embedded in a resin.

2. A process in accordance with claim 1 wherein said etchant is an acid effective in etching glass.

3. A process in accordance with claim 2 wherein said acid is hydrofluoric acid.

4. A process in accordance with claim 1 wherein said etchant is acidulated phosphate fluoride.

5. A process in accordance with claim 1 wherein said organo-functional silane is a silane selected from the group consisting of Vinyltrichlorosilane, Vinyltriethoxysilane, Vinyl-tris(beta-methoxyethoxy)silane, gamma-Methacryloxypropyltrimethoxysilane, beta-(3,4-Epoxycyclohexyl)ethyltrimethoxysilane, gamma-Glycidoxypropyltrimethoxysilane, gamma-Aminopropyltriethoxysilane, and N-beta-(aminoethyl)-gamma-aminopropyltrimethoxysilane.

6. A process in accordance with claim 1 wherein said resin is a composite resin.

7. A process in accordance with claim 1 wherein said resin is comprised of a microfill resin.

8. A process in accordance with claim 1 wherein said resin is comprised of a macrofill resin.

9. A process in accordance with claim 1 wherein said glass fiber material is in the form of a uniform mesh.

10. A process in accordance with claim 1 wherein said glass fiber material is in the form of a random mesh.

11. A process in accordance with claim 1 wherein said glass fiber material is in the form of a woven thread or rope.

12. An article of manufacture, comprising:
    a material for us in dental processes involving the reconstruction or stabilization of one or more teeth comprising an etched glass fiber material treated with an organo-functional silane.

13. A material in accordance with claim 12 wherein said fiber glass material is in the form of a uniform mesh.

14. A material in accordance with claim 12 wherein said fiber glass material is in the form of a random mesh.

15. A material in accordance with claim 12 wherein said fiber glass material is in the form of a woven thread or rope.

16. A material in accordance with claim 12 wherein said organo-functional silane is selected from the group consisting of Vinyltrichlorosilane, Vinyltriethoxysilane, Vinyl-tris(beta-methoxyethoxy)silane, gamma-(Methacryloxypropyltrimethoxysilane, beta-(3,4-Epoxycyclohexyl)ethyltrimethoxysilane, gamma-Glycidoxypropyltrimethoxysilane, gamma-Aminopropyltriethoxysilane, and N-beta-(aminoethyl)-gamma-aminopropyltrimethoxysilane.

* * * * *